(12) United States Patent
Flagan et al.

(10) Patent No.: US 6,567,157 B1
(45) Date of Patent: May 20, 2003

(54) FAST MIXING CONDENSATION NUCLEUS COUNTER

(75) Inventors: Richard C. Flagan, Pasadena, CA (US); Jian Wang, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 232 days.

(21) Appl. No.: 09/688,411

(22) Filed: Oct. 12, 2000

Related U.S. Application Data

(60) Provisional application No. 60/159,125, filed on Oct. 12, 1999.

(51) Int. Cl.[7] .................................................. G01N 1/26
(52) U.S. Cl. ........................ 356/37; 356/335; 356/440; 73/865.5; 73/28; 73/31.02; 73/863.21
(58) Field of Search ........................ 356/37, 335, 440; 73/28, 31.02, 863.21, 865.5

(56) References Cited

U.S. PATENT DOCUMENTS

| | | | |
|---|---|---|---|
| 3,806,248 A | | 4/1974 | Sinclair ........................ 356/37 |
| 5,596,136 A | | 1/1997 | Flagan et al. .............. 73/28.04 |
| 5,606,112 A | | 2/1997 | Flagan et al. .............. 73/28.04 |
| 5,675,405 A | * | 10/1997 | Schildmeyer et al. ........ 356/339 |
| 5,872,622 A | * | 2/1999 | Schildmeyer et al. ........ 356/339 |
| 5,903,338 A | * | 5/1999 | Mavliev et al. ............. 356/338 |
| 5,922,976 A | | 7/1999 | Russell et al. ............. 73/865.5 |
| 6,003,389 A | | 12/1999 | Flagan et al. ............. 73/865.5 |
| 6,051,189 A | | 4/2000 | Wick et al. .............. 422/82.01 |

FOREIGN PATENT DOCUMENTS

| | | |
|---|---|---|
| EP | 0 242 564 | 10/1987 |
| WO | WO 99/02957 | 1/1999 |

OTHER PUBLICATIONS

Agarwal, J.K. and Sem, G.J., "Continuous Flow, Single–particle Counting Condensation Nucleus Counter", J. Areosol Sci., (1980), vol. 11, pp. 343–357.

Bartz, H., Fissan, H., and Liu B.Y.H., "A New Generator for Ultrafine Aerosols Below 10–NM", Aerosol Sci. Technol., (1987), vol. 6, pp. 163–171.

Brink, H.M.T., Plomp, A., Spoelstra, H., and van de Vate, J.F., "A High–Resolution Electrical Mobility Aerosal Spectrometer (MAS)", J. Aerosol Sci., (1983), vol. 14, pp. 589–597.

Fissan, H.J., Helsper, C., and Thielen, H.J., "Determination of Particle Size Distributions by Means of an Electrostatic Classifier", J. Aerosol Sci., (1983), vol. 14, pp. S354–357.

Knutson, E.O. and Whitby, K.T., "Aerosol Classification by Electric Mobility: Apparatus, Theory and Applications", J. Aerosol Sci., (1975), vol. 6, pp. 443–451.

(List continued on next page.)

*Primary Examiner*—John R. Lee
*Assistant Examiner*—Zia R. Hashmi
(74) *Attorney, Agent, or Firm*—Christie, Parker & Hale, LLP

(57) ABSTRACT

A fast mixing condensation nucleus counter useful for detecting particles entrained in a sample gas stream is provided. The fast mixing condensation nucleus counter comprises a detector and a mixing condensation device having a mixing chamber adapted to allow gas to flow from an inlet to an outlet, wherein the outlet directs the gas flow to the detector. The mixing chamber has an inlet for introducing vapor-laden gas into the chamber and at least one nozzle for introducing a sample gas having particles entrained therein into the chamber. The inlet and nozzle are arranged such that the vapor-laden gas and sample gas mix turbulently. The mixing chamber is configured such that the particles flow through the mixing chamber at a substantially uniform relative velocity.

28 Claims, 10 Drawing Sheets

OTHER PUBLICATIONS

Wang, S.C. and Flagan, R.C. "Scanning Electrical Mobility Spectrometer", J. Aerosol Sci., (1989), vol. 20, pp. 1485–1488.

Ahn, Kang–Ho, et al; *Particle Activation and Droplet Growth Processes in Condensation Nucleus Counter—I. Theoretical Background*; J. Aerosol Sci, 1990, pp. 249–261, vol. 21, No. 2, Pergamon Press: Great Britain.

Ahn, Kang–Ho, et al.; *Particle Activation and Droplet Growth Processes in Condensation Nucleus Counter—II. Experimental Study*, J. Aerosol Sci., 1990, pp. 263–275. vol. 21, No. 2, Pergamon Press: Great Britain.

Kesten, J. et al; *Calibration of a TSI Model 3025 Ultrafine Condensation Particle Counter*; Aerosol Science and Technology, 1991, pp. 107–111, vol. 15, Elsevier Science.

Kousaka, Yasuo, et al; *Activation of Ultrafine Particles by Supersaturation in Condensational Process*; Part. Charact. 2; Apr. 1985, pp. 119 123.

Kousaka, Y. et al; *Development of a Mixing Type Condensation Nucleus Counter*; 1982; pp. 231–240; vol. 13, No. 3, Pergamon Press Ltd.: Great Britain.

Kousaka, Yasuo; *Evaluation of High Flow Rate Mixing Type CNC*; 1991; pp. 359–364; vol. 46, No. 4.

Liu, B.Y.H., et al; *Intercomparison of Different "Absolute" Instruments for Measurement of Aerosol Number Concentration*; J. Aerosol Sci.; 1982; pp. 429–450; vol. 13, No. 5; Pergamon Press: Great Britain.

Richardson, R.J., et al; *Developments in 30 Angstrom Particle Detection for Ultraclean Gas System*; J. Aerosol Sci.; 1990; pp. S575–S578; vol. 21, Suppl. 1; Pergamon Press: Great Britain.

Russell, Lynn M. et al; *Asymmetric Instrument Response Resulting from Mixing Effects in Accelerated DMA–CPC Measurements*; Aerosol Science and Technology; 1995; pp. 491–509; vol. 23; Elsevier, Inc.

* cited by examiner

FAST MIXING CONDENSATION NUCLEUS COUNTER

CROSS-REFERENCE TO RELATED APPLICATION(S)

This application is based on U.S. Application No. 60/159,125, filed Oct. 12, 1999, the disclosure of which is incorporated by reference.

STATEMENT REGARDING FEDERALLY SPONSORED RESEARCH

The U.S. Government has certain rights in this invention pursuant to grant N0014-96-1-0119 awarded by the U.S. Office of Naval Research.

FIELD OF THE INVENTION

The present invention is directed to a fast mixing condensation nucleus counter for use in determining the physical characteristics of aerosol particles.

BACKGROUND OF THE INVENTION

Atmospheric particles influence climate change, radiative transfer, visibility, and air quality. Atmospheric aerosols include particles that are emitted directly to the atmosphere and those that are formed in the atmosphere by the reactions of gaseous pollutants and certain natural compounds. At high concentrations, they become the haze that reduces visibility a becomes a health hazard. Aerosols also play an important role in the global atmosphere. They scatter sunlight back to space, producing a cooling effect that partially offsets the warming induced by greenhouse gases such as $CO_2$.

Aerosol measurements characterize the size, concentration and composition of particles suspended in the atmosphere. The ability to measure the concentration and size distribution of fine particles is essential to the understanding of the dynamics of aerosols in the atmosphere, in combustion systems, or in technological applications. The importance of characterizing fast transient aerosols has increased in recent years. For example, rapid transients in aerosol systems can arise due to dynamic response, such as in diesel engine particle emissions, or as a result of high speed traversing through different air masses, commonly a problem in airborne measurements. A continuing focus of aerosol research, then, is the development of measurement methods that have the time and size resolution necessary to resolve rapid aerosol dynamics in the atmosphere and in technological systems.

Detection and analysis of aerosols using a condensation nucleus counter (CNC) is well known. The CNC is also used as the primary detector for obtaining particle size distributions, for example in scanning electrical mobility spectrometers (SEMS), also known as scanning mobility particle sizers (SPMS). However, traditional CNC designs have slow detector response times, limiting the speed at which particle size distributions can be obtained, and thus rendering them impractical for obtaining time sensitive particle size distributions.

The condensation nucleus counter detects particles by condensing a vapor on the particles to grow them to large enough size that they can be counted optically. This measurement involves four steps: i) the production of sufficient quantities of vapor; ii) creation of the supersaturation necessary to activate the particles; iii) maintenance of the particles in the supersaturated state long enough to grow to detectable size; and iv) detection of the grown particles. The time required for a CNC to respond to changes in the aerosol concentration is constrained by the sum of the relevant times.

Another problem with these traditional CNCs is that stable flow recirculations are created in these systems. Stable flow recirculations operate to randomly trap some of the sample particles within the CNC. Thus, while some particles immediately exit the mixing region and enter the detector, other particles continue to recirculate inside the CNC and randomly exit at some later time, introducing an exponentially decaying distribution of delays between the time a particle enters the CNC and when it is detected. This was not a problem for early uses of CNCs, but has important consequences when such detectors are used for time sensitive measurements. In particular, the distribution of delay times smears scanning DMA size distribution measurements so the full potential of SEMS systems has not yet been realized. These stable flow recirculations create mixing and detection delays of up to 1 s, making scans shorter than 3 s impractical in these CNC systems.

In these traditional CNC designs, the aerosol sample is first passed through a saturation chamber wherein a sufficient quantity of vapor-laden gas is produced, and then to a condensation chamber for supersaturation and growth. In later designs, the sample aerosol bypasses the saturation chamber and is fed directly into the condensor where it mixes, under laminar flow conditions, with a pre-saturated flow of gas from the saturation chamber. This simple plumbing change eliminates the time delay associated with vapor production step above, and increases the detection speed of the CNC dramatically. For example, in a CNC using the original design, such as the TSI Model 3010, a typical particle size distribution scan (with data inversion to correct for smearing of the data) can be taken in 30 to 45 s. Meanwhile, scans up to 10 times faster can be obtained with ultrafine CNC (UCNC) devices, such as the TSI Model 3025, utilizing the saturation chamber bypass design.

While scanning times are faster in these UCNC systems, such UCNC devices generally have a very small aerosol flow rates, up to 33 times smaller than the standard CNCs, reducing the count rate obtainable with these detectors and making such devices practical only for aerosols with extremely high number concentrations or long sample times. This is particularly true at the low end of the particle size distribution where the charging efficiency of the spectrometer is low. As a result of the low signal strength of such devices, particles in a single mobility channel must be scanned for a longer time, either by reducing the scan rate, or by summing the counts acquired during a number of scans. While either of these solutions will increase count rates, both of these solutions also increase the length of time needed to obtain a scan, rendering the device less than ideal for obtaining particle size distributions where small fast transients are involved.

An alternative design for continuous-flow CNCs is the mixing CNC (MCNC). In this instrument a cold aerosol flow is mixed with a comparable flow of hot, vapor-laden gas. The mixed gas then passes from the mixing chamber into a chamber that provides sufficient residence time for the supersaturated particles to grow to optically detectable sizes. In these MCNC systems, rapid, nearly adiabatic mixing is facilitated by making the mixing region turbulent. Turbulent mixing can achieve compositional homogeneity quickly and without the use of a cooler. However, until now, large mixing chamber volumes have been employed to prevent thermophoretic deposition of the aerosol particles in the mixing chamber. The large mixing chamber volumes employed in these MCNC systems also create stable recirculation zones within the mixing chamber, resulting in long residence times for the aerosol in the mixing chamber rendering these MCNCs too slow for use as a DMA detector.

Accordingly, a need exists for a system that provides a fast response CNC which would allow accelerated SEMS measurements by reducing the residence time of aerosol particles in the system while maintaining high sample flow rates that enable high count rates by the detector.

SUMMARY OF THE INVENTION

The present invention is directed to a fast mixing condensation nucleus counter (FMCNC), for use in obtaining particle size distributions of fast transient aerosol systems over a wide range of particle sizes. This invention utilizes the turbulent mixing technology of the MCNC systems to provide fast particle growth and high sample flow rate and signal strength, but restricts the size of the mixing chamber to minimize the detector delay associated with traditional MCNC systems. This invention is also directed to novel methods for obtaining particle size distributions of fast transient aerosol systems over a wide range of particle sizes using the FMCNC of the invention.

In one embodiment, the invention is directed to a fast mixing condensation nucleus counter comprising a detector and a mixing condensation device having a mixing chamber adapted to allow gas to flow within it along a preselected path to an outlet, wherein the outlet directs the gas flow to the detector. The mixing chamber has an inlet for introducing vapor-laden gas into the chamber and at least one nozzle for introducing a sample gas having particles entrained therein into the chamber. The inlet and nozzle are arranged such that the vapor-laden gas and sample gas mix turbulently. The mixing chamber is configured such that the particles are distributed throughout the mixing chamber and move through the mixing chamber at a substantially uniform relative velocity. In an alternative statement of the invention, the mixing chamber is configured such that adjacent particles within the mixed gas flow move through mixing condensation chamber substantially together.

The fast mixing condensation nucleus counter also comprises a growth tube positioned between the outlet of the mixing chamber and the detector, wherein the growth tube is adapted to allow the mixture of vapor-laden gas and sample gas to flow along a preselected path to the detector such that the mixture is given sufficient time to allow the vapor-laden gas to condense on the particles entrained in the sample gas and grow the particles large enough for optical detection by the detector.

In a preferred embodiment, the mixing chamber comprises two nozzles positioned opposite one another (antipodal) and transverse to the vapor-laden gas inlet. In this embodiment a gas distribution manifold evenly divides the sample gas flow between the two nozzles.

In another embodiment, the invention is directed to a fast mixing condensation nucleus counter where the counter comprises a mixing chamber as described above, a gas distribution manifold and a saturation chamber. The gas manifold is positioned between the source of sample gas and the saturation chamber, and the saturation chamber is positioned between the gas manifold and the mixing chamber. The gas manifold is adapted to evenly divide the sample gas flow into two gas flows and direct one flow into the saturation chamber and one flow directly into the nozzle of the mixing chamber. The gas flowing into the saturation chamber interacts with a vaporized working gas to produce a vapor-laden gas which is then directed into the inlet of the mixing chamber. In a preferred embodiment, the saturation chamber comprises a packed bed reservoir of vaporized working gas. In another preferred embodiment, the saturation chamber also comprises a temperature control apparatus, where the temperature control apparatus maintains the temperature of the vapor-laden gas at a first temperature and where the sample gas has a second temperature, and wherein the first temperature is greater than the second temperature such that when the vapor-laden gas and the sample gas mix in the mixing chamber, the hot vapor-laden gas condenses on the cold particles of the sample gas before reaching the detector. In another preferred embodiment the temperature of the vapor-laden gas is maintained at between 60 and 90° C. and the temperature of the sample gas is maintained at room temperature.

In yet another preferred embodiment, the saturation chamber further comprises a filter positioned at the inlet to the saturation chamber such that the sample gas entering the saturation chamber is filtered to remove any particles entrained therein.

In yet another preferred embodiment, the fast mixing condensation nucleus counter further comprises a second gas manifold positioned between the filter and the saturation chamber. The gas manifold is adapted to divide the gas flowing through the filter into two gas flows, where one gas flow is directed to the saturation chamber and the other gas flow is directed through a bypass, and wherein the outlet of the saturation chamber and bypass are configured such that the flows mix prior to entering the inlet of the mixing chamber. In this embodiment of the invention, the division of the sample gas flow can be variably controlled such that by changing the ratio of gas flowing into the saturation chamber, the ratio of the vapor in the vapor-laden gas entering the mixing chamber can be adjusted.

In still another embodiment, the invention is directed to a fast mixing condensation nucleus counter wherein the sample gas source comprises calibration source comprising a nebulizer for producing a constant ultrafine sample gas flow rate and a tube furnace in fluid communication with the outlet of the nebulizer, wherein the tube furnace heats the sample gas to a constant furnace temperature. The tube furnace also having a furnace quencher wherein the quencher provides a source of filtered air such that the filtered air is injected into the outlet of the tube furnace at a specified injection rate to cool the heated gas. The sample gas source also comprising a differential mobility analyzer (DMA) classifier for sorting particles based on their size to produce a monodisperse ultrafine sample gas of specified particle size. In a preferred embodiment, the DMA classifier is either a cylindrical or radial DMA classifier. In another preferred embodiment, the sample gas source also comprises a charger disposed between the sample inlet and the inlet of the classifier. In yet another preferred embodiment, the charger employs a radioactive source, such as, a $^{210}Po$.

In still yet another embodiment, the invention is directed to a method for detecting the particle size distribution of particles entrained in a sample gas. The method comprises analyzing a sample gas using a fast mixing condensation nucleus counter as described above. In another embodiment, the invention is directed to a method for detecting the particle size distribution of particles entrained in a sample gas using the FMCNC described above in a fast scan mode.

BRIEF DESCRIPTION OF THE DRAWINGS

These and other features and advantages of the present invention will be better understood by reference to the following detailed description when considered in conjunction with the accompanying drawings wherein:

DETAILED DESCRIPTION OF THE INVENTION

Figure 1:
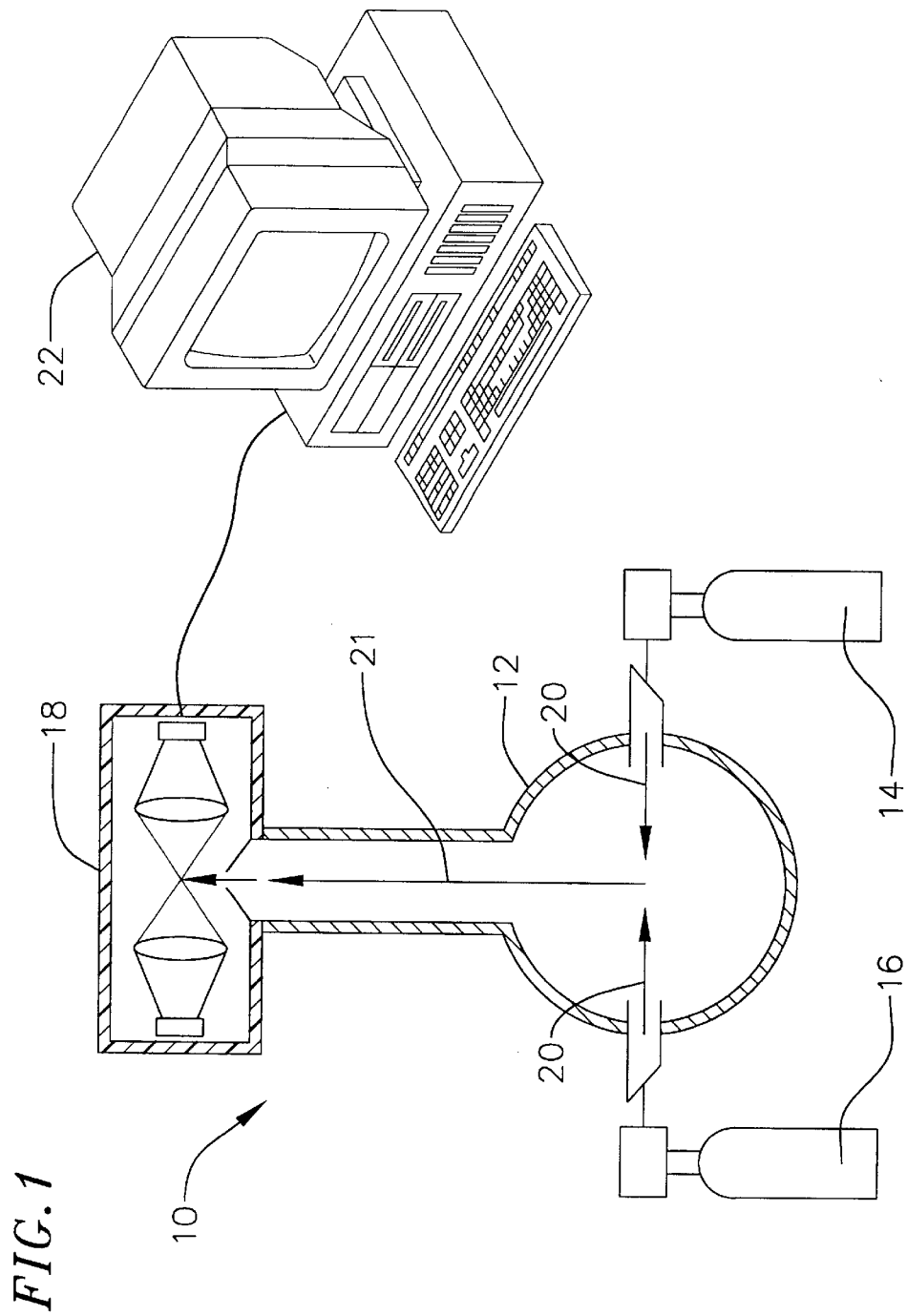
FIG. 1 is a schematic view of an embodiment of the fast mixing condensation nucleus counter according to the invention.

The present invention is directed to a condensation nucleus counter designed to ensure rapid, homogenous, and adiabatic mixing of a gas sample with a vapor-laden gas, the condensation nucleus counter of the present invention herein called a fast mixing condensation nucleus counter (FMCNC). The FMCNC of the present invention being designed to detect particles entrained in a sample gas stream. In one embodiment, as shown in FIG. 1, the FMCNC 10 of the invention comprises a mixing chamber 12, in fluid communication with a sample gas source 14, a vapor-laden gas source 16, and a detector 18. Gas flows 20 are introduced into the mixing chamber 12 from the sample gas source 14 and the vapor-laden gas source 16 such that they turbulently mix in the mixing chamber 12. The combined gas flow 21 then passes through the mixing chamber 12 and into the detector 18, where the combined gas flow 21 is analyzed and the results output to a suitable monitor 22. Any device having the ability to detect particles entrained within the combined gas flow 21 can be used as a detector 18 and monitor 22, for example, an optical particle detector in signal communication with a computer.

Figure 2:
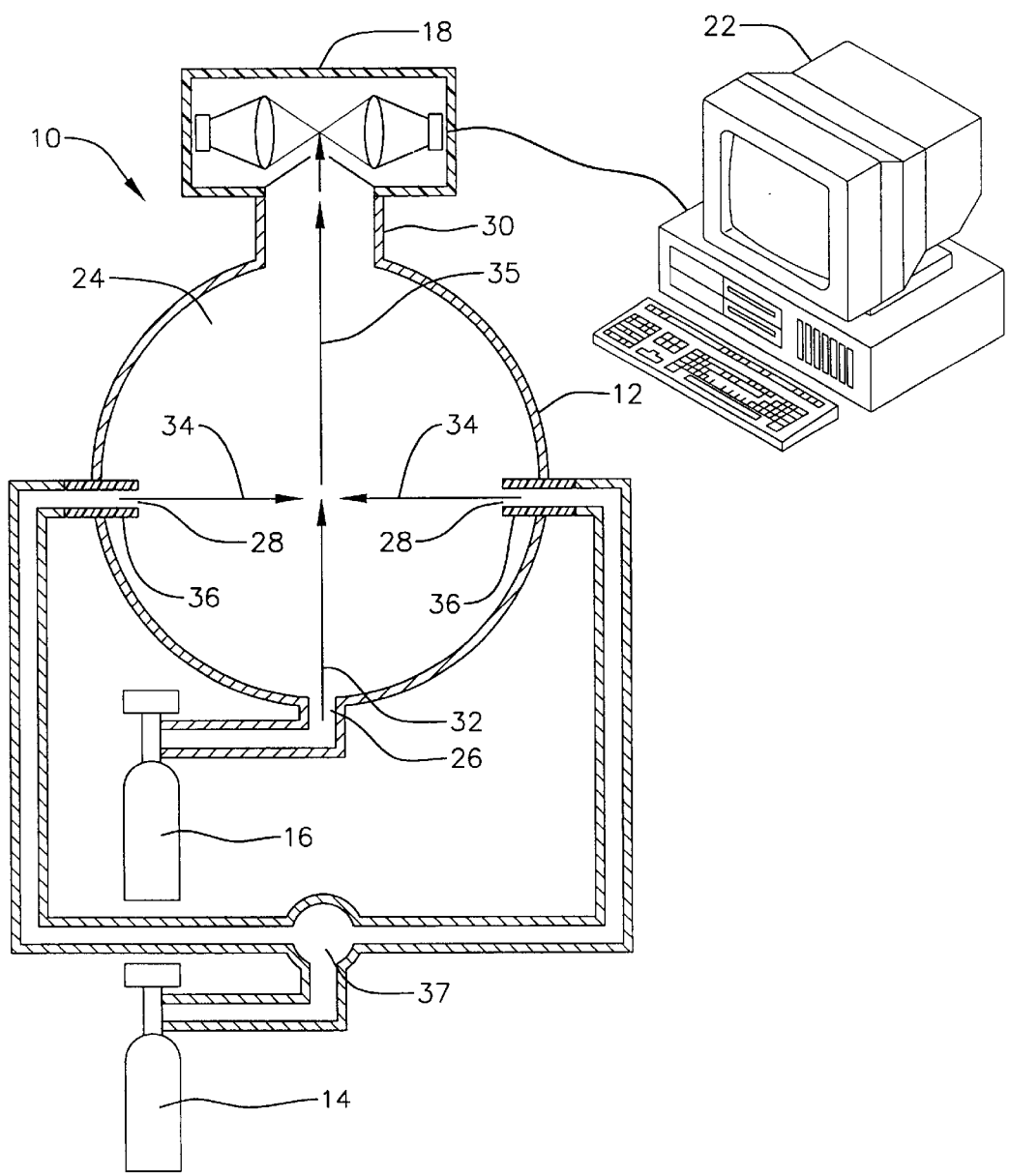
FIG. 2 is a schematic view of an embodiment of the mixing chamber according to the present invention.

The mixing chamber 12, as shown in detail in FIG. 2., defines an inner cavity 24, having an inlet 26 in fluid communication with the vapor-laden gas source 16, a set of nozzles 28 in fluid communication with the sample gas source 14, and an outlet 30 in fluid communication with the detector 18. The nozzles 28 and the inlet 26 are constructed such that the vapor-laden gas flow 32 and the sample gas flow 34 turbulently interact to create a mixture within the mixing chamber 12. In the embodiment shown, the nozzles 28 are aligned antipodal to each other and transverse to the inlet 26, however, any other configuration which produces turbulent interaction of the vapor-laden gas flow 32 and the sample gas flow 34 could also be used. For example, the two nozzles 28 and the inlet 26 could be aligned in opposing tangential trajectories, such that the sample gas flow 34 circulates in one of either a clockwise or counter clockwise direction within the mixing chamber 12 and the vapor-laden gas flow 32 circulates in the opposite direction, creating turbulent mixing of the two flows. Additionally, while the pictured embodiment comprises two nozzles 28, any suitable combination and construction of at least one nozzle or multiple nozzles 28 can be used, so long as the nozzle(s) 28 are constructed so that turbulent mixing of the vapor-laden gas flow 32 and the sample gas flow 34 occurs.

Mixing of the vapor-laden gas flow 32 and the sample gas flow 34 is enhanced by turbulently mixing. Turbulence also helps offset the difficulty expected in trying to create supersaturation in a gas stream via conductive-cooling for a working fluid with a high molecular diffusivity such as water. Supersaturation in a laminar-flow conductive-cooling scheme is limited by the relative molecular and thermal diffusivities of the sample gas flow 34 and the vapor-laden gas flow 32 for which supersaturation is being generated. Turbulent flow makes the achieved supersaturation more dependent on the turbulent flow structure itself, rather than on the molecular and thermal diffusivities. Turbulent flow is created by aligning and sizing the inlet 26 and nozzles 28 through which the vapor-laden flow 32 and sample gas flow 34 respectively enter the inner cavity 24, such that the diameter of the inlet 26 and nozzles 28 result in a turbulent Reynolds number for the flows 32 and 34 as it enters mixing chamber 12. Generally, Reynolds numbers of less than 2200 are laminar for cylindrical pipe flow. For impinging nozzles gas flows such as 32 and 34, non-laminar flow likely occurs at even lower Reynolds numbers. As the gas mixture moves from the inlet 26 and nozzles 28 of the mixing chamber 12 to and through the outlet 30, the entrained particles act as nucleation sites for condensation due to the state of supersaturation within mixing chamber 12. The grown particles 35 then pass through outlet 30 and into particle detector 18.

The nozzles 28 and inlet 26 are both made of a material that is generally rigid, such as, for example, stainless steel. If desired to prevent thermal coupling of the vapor-laden gas flow 32 and the sample gas flow 34, the inlet 26 and the nozzles 28 can be coupled to the mixing condensation chamber through individual insulating tubings 36. The insulating tubings 36 thermally separate the "hot side" (vapor-laden gas source 16) of the FMCNC 10 from the "cold side" (sample gas source 14) of the FMCNC 10. The insulating tubings 36 effectively isolate the vapor-laden gas inlet 26 and the nozzles 28 from the inner cavity 24. Although a material such as Ultem is preferably used for the insulating tubings 36 due to its high-temperature properties, the insulating tubings 36 can be made of any material that is generally thermal insulating. Preferably the vapor-laden gas inlet 26 has an internal diameter ranging from 0.25 to 1.0 cm, more preferably of about 0.48 cm, even more preferably, the inlet 26 has an inner diameter about the same as the cross-section of the inner cavity 24. Preferably the nozzles 28 have an internal diameter ranging from 0.1 to 1.0 mm, more preferably ranging from 0.5 to 0.8 mm, still more preferably of about 0.7 mm. It will be understood though that the internal diameter can be any size such that the nozzle provides turbulent mixing characteristics without impaction of the gas particles.

To connect the sample gas source 14 to each of the nozzles 28, the FMCNC 10 also has a sample gas distribution manifold 37 adapted to allow gas to flow between the sample gas source 14 and the nozzles 28. The sample gas distribution manifold 37 is constructed to evenly divide the sample gas flow 34 into a plurality of flows, with each of the flows being directed to enter one of the nozzles 28. The sample gas distribution manifold 37 can be constructed in any suitable manner that would allow the sample gas flow 34 to reach the plurality of nozzles 28 of the mixing chamber 12.

The mixing chamber 12 is also made of a material that is generally rigid, such as, for example, stainless steel. The mixing chamber 12 is constructed such that the mixture created by the turbulently mixing gas flows 32 and 34 flow through the mixing chamber 12 from the inlet 26 and nozzles 28 to the outlet 30. The inner cavity 24 of the mixing chamber 12 is configured such that the particles entrained in the sample gas flow 34 move from the nozzles 28 to the outlet 30 at a substantially uniform relative velocity or such that adjacent particles move through the mixing chamber substantially together.

Any suitable design of the mixing chamber 12 may be used so long as the volume of the inner cavity 24 is restricted sufficiently to substantially eliminate those stable recirculation currents or dead zones that would cause the gas flows 32 and 34 to reside within the mixing chamber between the inlet 26 and nozzles 28 and the outlet 30 for longer than a small fraction of the total residence time in the FMCNC 10 between the mixing chamber 12 and the detector 18. Preferably the inner cavity 24 has a volume less than about 1.00 cm$^3$, more preferably less than about 0.85 cm$^3$.

Figure 3:
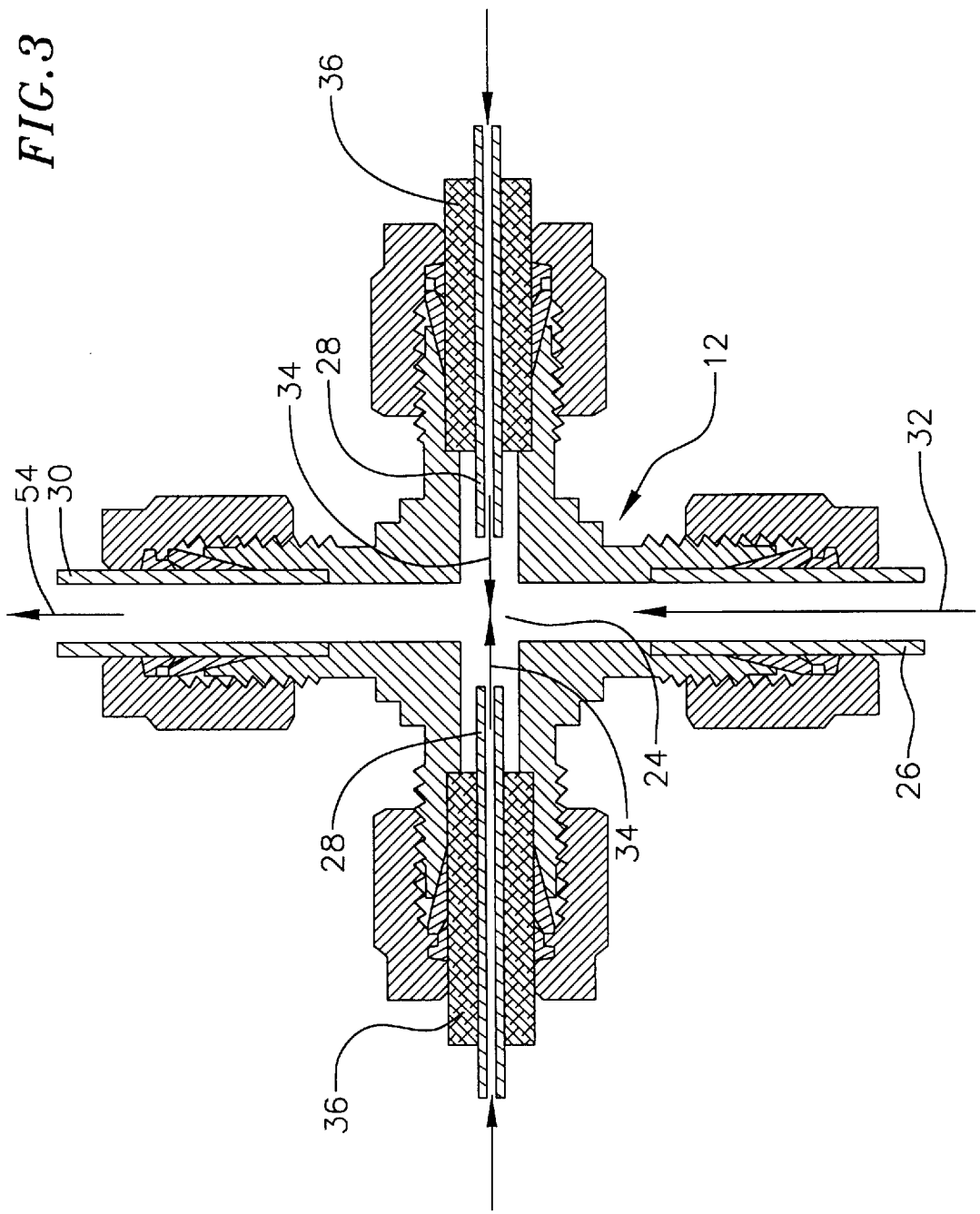
FIG. 3 is a cross-sectional view of an embodiment of the mixing chamber according to the invention.
Figure 4:
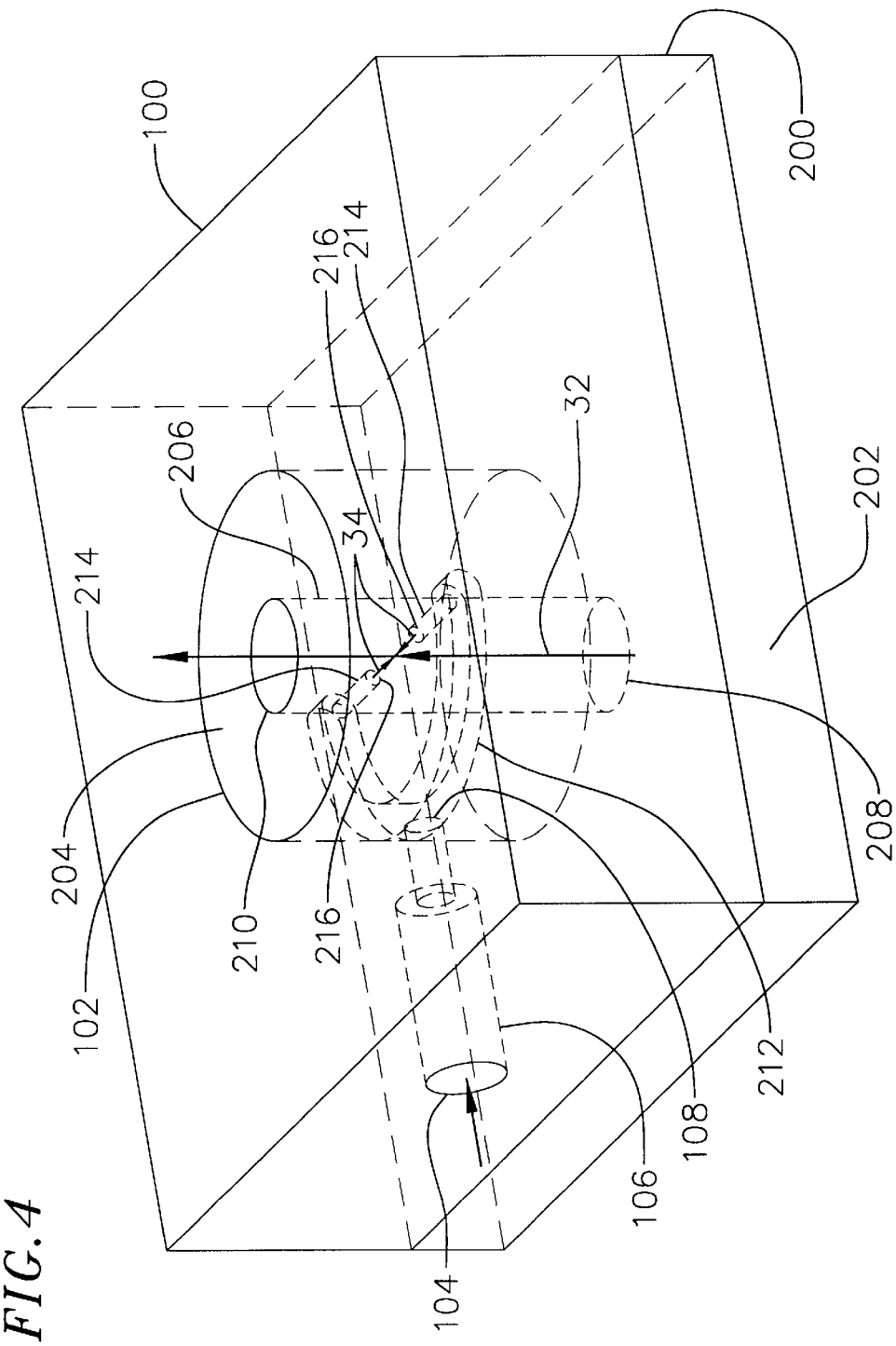
FIG. 4 is a schematic view of an alternative embodiment of the mixing chamber according to the invention.
Figure 5:
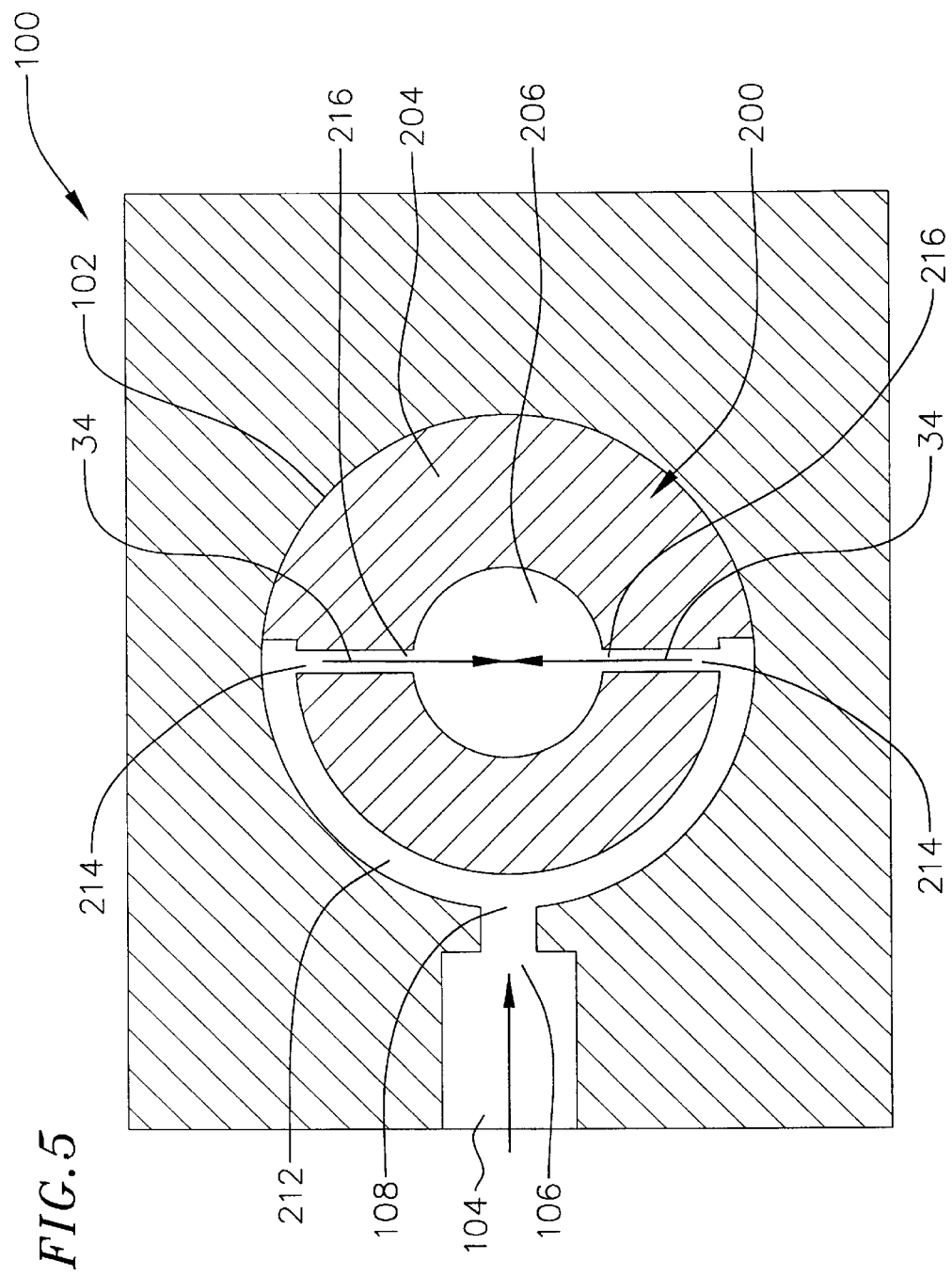
FIG. 5 is a cross-sectional view of the embodiment of the mixing chamber of the present invention as shown in FIG. 4.

FIGS. 3 to 5 show two possible embodiments of the mixing chamber 12 of the present invention. FIG. 3, illustrates a detailed view of a simple four-way cross embodiment of the mixing chamber 12 of the present invention. In this implementation, the mixing chamber 12 is constructed from a 0.25 inch tubular cross-shaped fitting manufactured by Swagelok. The sample gas flow 34 is divided into two flows, as described above, and introduced through nozzles 28 aligned antipodal to each other. The vapor-laden gas flow 32 is introduced into the mixing chamber 12 through the inlet 26 aligned transverse to the nozzles 28 and antipodal to the outlet 30. The inlet 26 has an internal diameter of 0.48 cm and the nozzles 28 have an internal diameter of 0.7 mm to ensure efficient turbulent mixing of the sample gas flow 34 with the vapor-laden gas flow 32. The nozzles 28 are thermally isolated from the rest of the mixing chamber 12 by the addition of the insulating tubings 36, which couple the nozzles to the mixing chamber 36. The total volume of the mixing chamber 12 is about 0.85 cm$^3$.

FIGS. 4 and 5 show another specific embodiment of the mixing chamber 12 of the present invention. As shown in FIG. 4, in this implementation, the mixing chamber 12 is constructed from first 100 and second 200 interlocking blocks. Block 100 comprises a generally solid metallic cube having a hollow cylindrical conduit 102 milled into its center point. Block 100 further has an inlet 104, which serves as an entrance to another hollow cylindrical passage 106 extending from the inlet 104 at the outer edge of the block 100, to an outlet 108 in fluid communication with the hollow cylinder 102 at the center of the block 100. The second block 200 comprises a generally solid cubic base 202 and a generally solid cylinder 204 extending perpendicularly out of the surface of the cubic base 202. The solid cylinder 204 comprises an inner hollow cylinder 206 having an inlet 208 and an outlet 210. The inner hollow cylinder 206 extends coaxially through the center of the solid cylinder 204 from the inlet 208, at the center point of the solid cubic base 202, to the outlet 210. A hollow channel 212 extends 180° around the circumference of the solid cylinder 204 and terminates at either end in nozzle conduits 214. The nozzle conduits 214 extend radially into the solid cylinder 204. The nozzle conduits 214 have nozzle outlets 216 aligned antipodal to each other that open into the inner hollow cylinder 206. The two blocks 100 and 200 interlock such that the generally solid cylinder 204 of block 200 extends into the hollow cylinder 102 of block 100. The solid cylinder 204 and the hollow cylinder 102 fit, such that an airtight seal is formed between the solid cylinder 204 and the hollow cylinder 102, and such that the outlet 108 of the conduit 106 is in fluid communication with the hollow channel 212. The airtight seal between blocks 100 and 200 may be improved by interposing an o-ring seal between the interacting faces of the blocks.

FIG. 5 shows a cross section of the fluid passage thus formed by the interlocked blocks 100 and 200. The inlet 104 is in fluid communication with the conduit 106 which in turn is in fluid communication with hollow channel 212 through outlet 108. Hollow channel 212 is in turn in fluid communication with nozzle conduits 214 which are in fluid communication with inner hollow cylinder 206 through nozzle outlets 216. In this embodiment, the sample gas flow 34 enters the device through inlet 104, flows through conduit 106, and is divided into two flows at outlet 108. One of the sample gas flows 34 travels clockwise around hollow channel 212 and the other sample gas flow travels counterclockwise around hollow channel 212. The sample gas flows 34 are then introduced through nozzle conduits 214 out of nozzle outlets 216 and enter the hollow inner cylinder 206 which serves as the mixing chamber 12. The vapor-laden gas flow 32 is introduced into the inner hollow cylinder 206 or mixing chamber 12 through the inlet 208 in the cubic base 202 of block 200, as shown in FIG. 4. The inlet 208 is aligned transverse to the nozzle outlets 216 and antipodal to the outlet 210. The sample gas flow 34 and the vapor-laden gas flow 32 mix in the inner hollow cylinder 206 and pass through the outlet 210 to the detector 18 beyond. The inlet 208 has an internal diameter of 0.45 cm and the nozzles 216 have an internal diameter of 0.057 cm to ensure efficient turbulent mixing of the sample gas flow 34 with the vapor-laden gas flow 32. The total volume of the mixing chamber 12 is about 0.087 cm$^3$. As described above, the nozzle outlets 216 can be thermally isolated from the rest of the inner hollow cylinder 206 if desired by the addition of the insulating tubings (not shown), which would couple the nozzle conduits 214 to the inner hollow cylinder 206.

Figure 6:
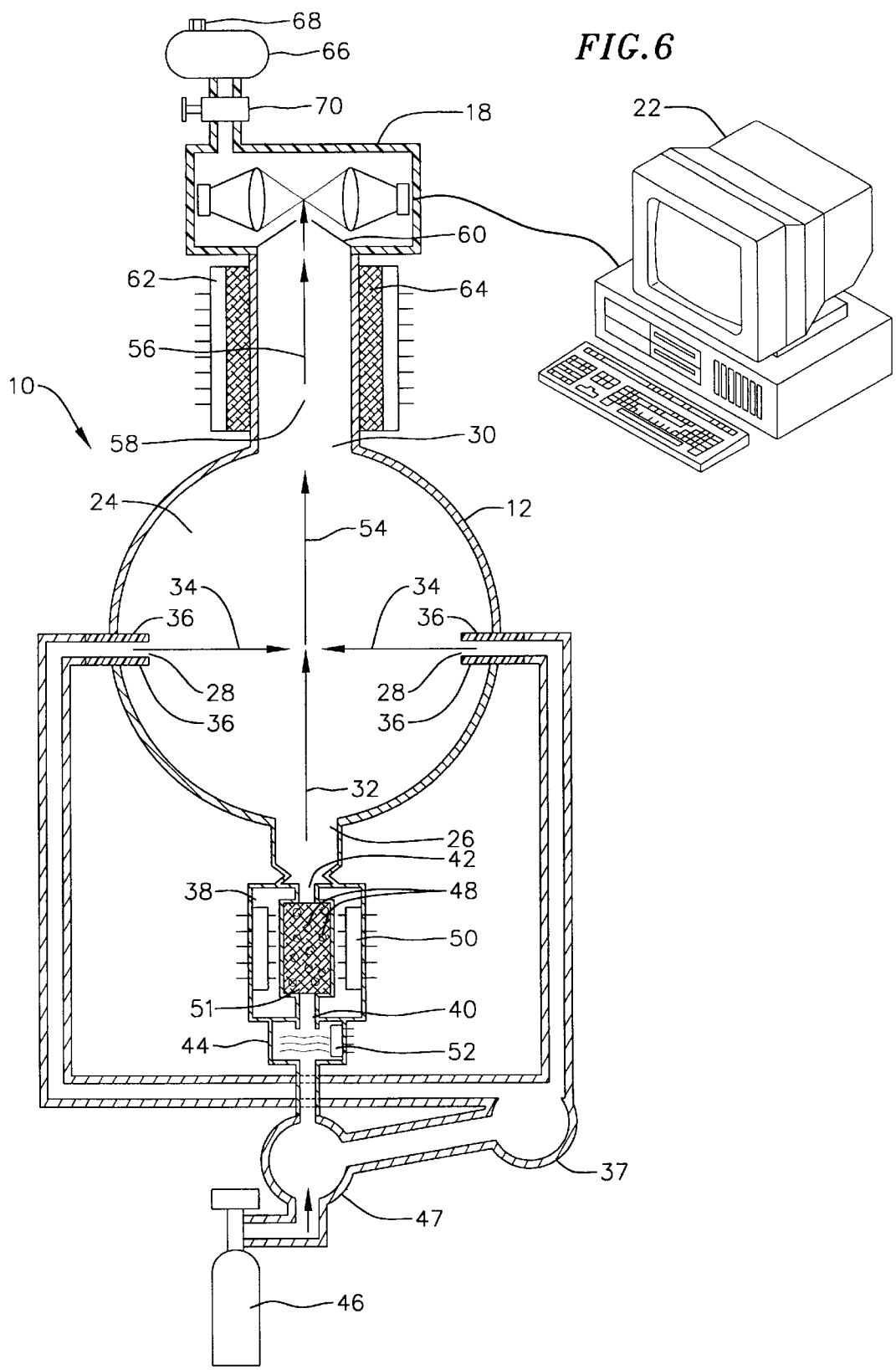
FIG. 6 is a schematic view of an alternative embodiment of the fast mixing condensation nucleus counter according to the invention.
Figure 7:
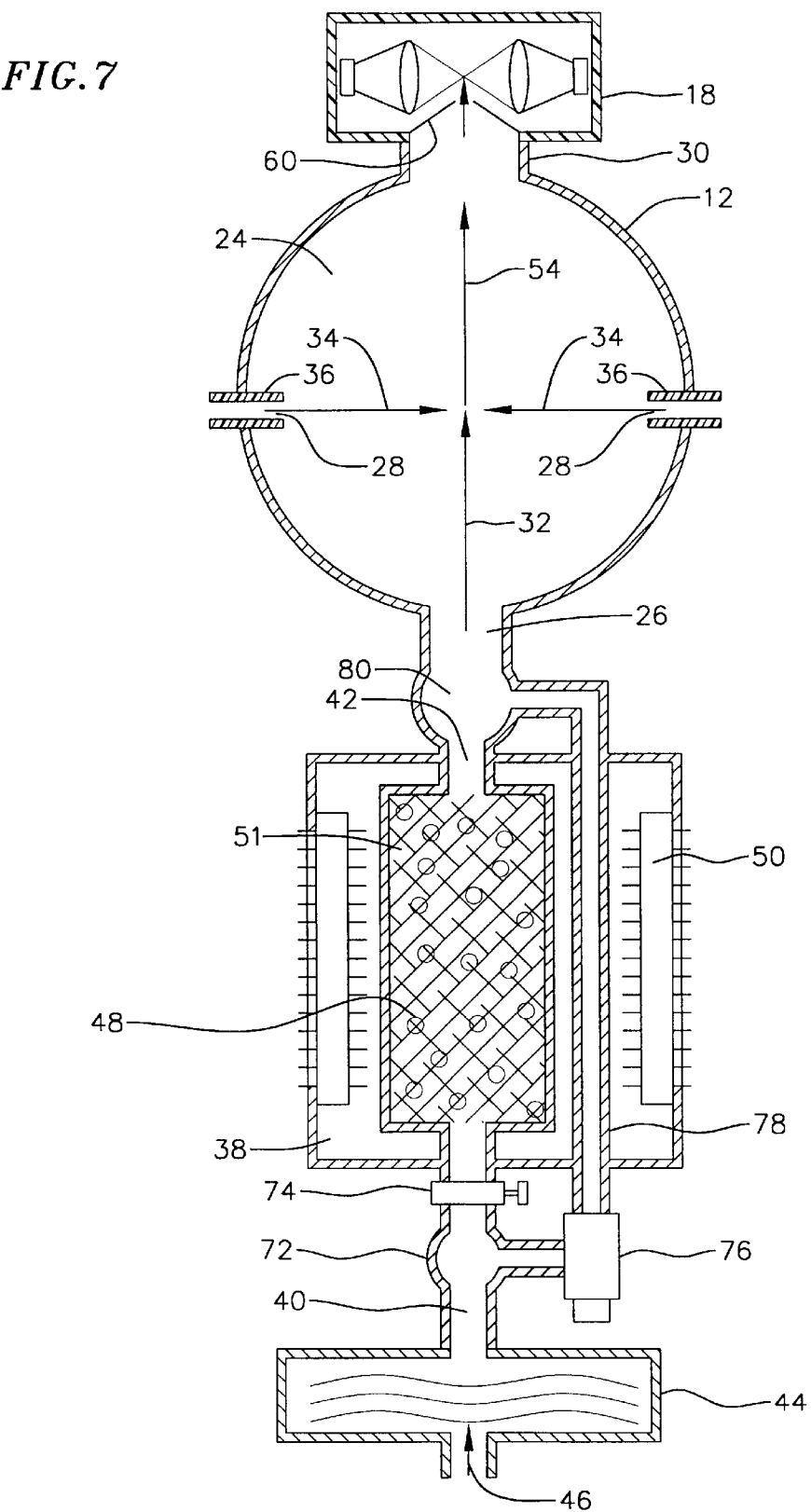
FIG. 7 is a schematic view of another alternative embodiment of the fast mixing condensation nucleus counter according to the invention.
Figure 8:
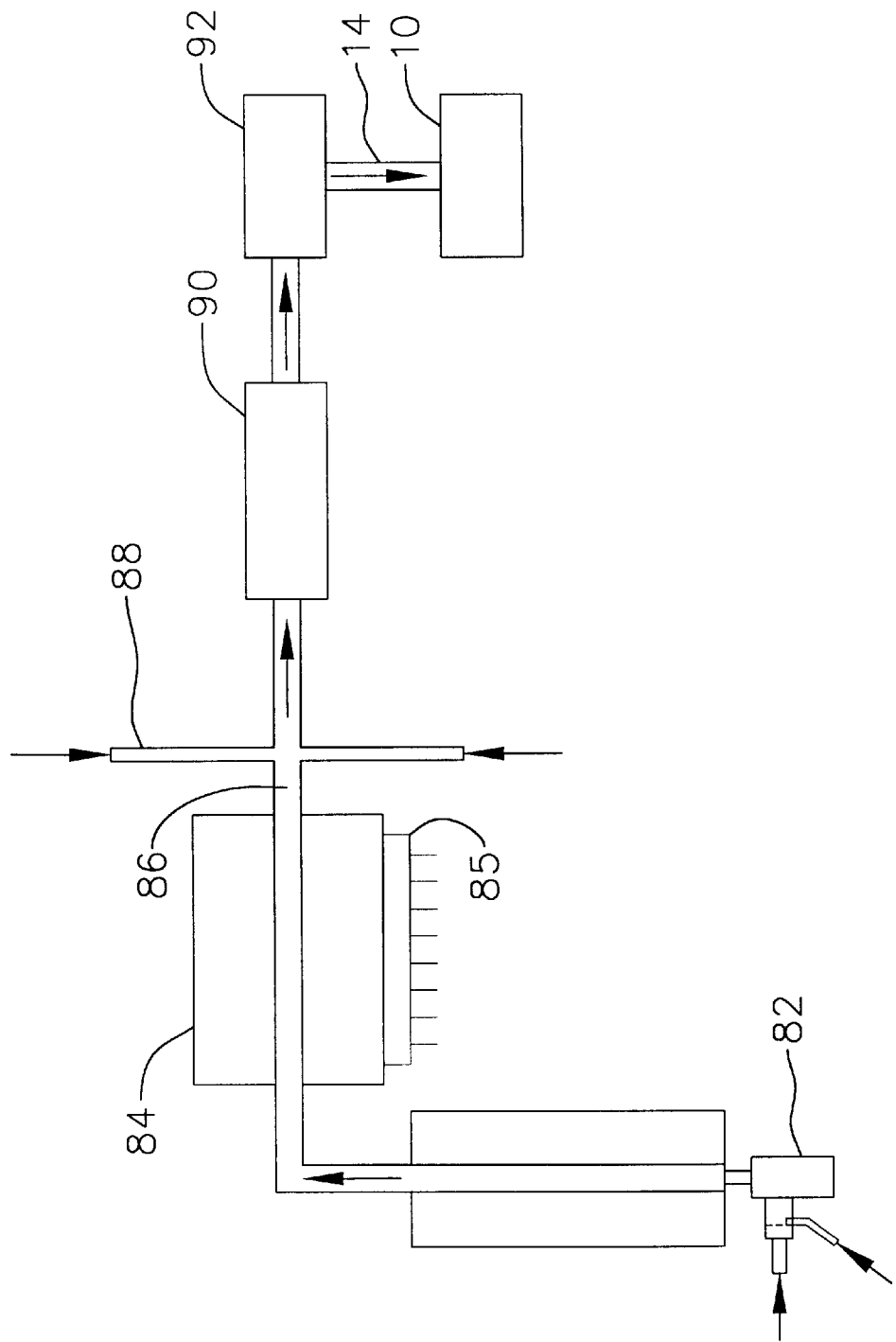
FIG. 8 is a schematic view of yet another alternative embodiment of the fast mixing condensation nucleus counter according to the invention.

Several alternative embodiments of the fast mixing condensation nucleus counter 10 of the present invention are shown in FIGS. 6 to 8. The vapor-laden gas source 14 as shown in FIG. 6 comprises a saturation chamber 38 having an inlet 40 and an outlet 42. The saturation chamber inlet 40 is in fluid communication with a saturation filter 44 such that an untreated gas flow 46 runs through the saturation filter 44, enters the saturation chamber 38, interacts with a vaporized working fluid 48 held therein, and exits the saturation chamber outlet 42 as a vapor-laden gas flow 32.

In the embodiment shown in FIG. 6, an untreated gas distribution manifold 47 is positioned at the entrance to the saturation filter 44. The untreated gas distribution manifold 47 is constructed to evenly divide the untreated gas flow 46 into a plurality of flows, with one of the flows being directed to enter the saturation filter 44 and from there the saturation chamber 38, and one of the flows being directed to bypass the saturation chamber and enter the mixing chamber 12 directly through the nozzles 28. The untreated gas distribution manifold 47 can be constructed in any suitable manner that would allow the sample gas to be distributed between the saturation chamber 38 and the nozzles 28.

In the embodiment described herein, butanol is used as the working fluid 48; however, any suitable working fluid may be used provided the working fluid can be vaporized in the saturation chamber 38 and condensed onto the particles entrained within the sample gas flow 34 prior to reaching the detector 18. For example, common working fluids include: dibutylphthalate (DBP), dioctylsebacate (DOS), Multifluor APF-175 (Air Products and Chemicals, Inc. Allentown, Pa.), or water. However, those skilled in the art of CNCs will recognize that many fluids could be suitable for use as the working fluid 48, so long as it is chemically inert (would not react or decompose when heated) and the vapor pressure at different temperatures is well known. The saturation chamber outlet 42 is in fluid communication with the mixing chamber 12 such that the vapor-laden gas flow 32 exits the saturation chamber and then enters the mixing chamber 12.

The saturation chamber 38 is in thermal communication with a temperature controller 50 which heats the saturation chamber 38 and the vapor-laden gas flow 32 therein to a specified vapor-laden gas temperature $T_1$. Any first temperature $T_1$ sufficient to cause saturation of the untreated gas stream 46 may be used. The actual appropriate range for the vapor-laden gas temperature $T_1$ depends upon the working fluid 48 used in the FMCNC 10. Preferably, a first temperature is chosen which aides the saturation process within saturation chamber 38 and later the condensation process within the mixing condensation chamber 12. The saturation chamber temperature must exceed a minimum value to produce supersaturation according to the equation:

$$\Delta\chi_v = \chi_v - \chi_{sat}$$

where $\chi_v$ is the actual vapor mole fraction in the mixing chamber 12 at a particular time, $\chi_{v,sat}$ is the vapor mole fraction needed to achieve saturation and $\Delta\chi_v$ is the excess vapor mole fraction. The present invention uses a temperature $T_1$ which yields a large excess vapor mole fraction, for example, when butanol is the working fluid the temperature $T_1$ can range from 40 to 90° C., more preferably from 65 to 85° C., still more preferably about 80° C. However, other saturation temperatures may be used depending on the working fluid utilized, for example, for water a temperature of 60 to 80° C., and for Dibutylphthalate (DBP) a temperature of 100–135° C. Temperatures outside this range could also be used within appropriate changes in flow rates, mixing conditions, or growth chamber temperature. There are a number of means by which one can heat the saturation chamber 38. In one embodiment of the present invention, shown in FIG. 6, a cartridge-type electrical temperature controller 50 is inserted into the saturation chamber. FireRod electrical heaters manufactured by Watlow are an example of this type of heater.

Those skilled in the art of CNC's recognize that there are a number of methods one can use to saturate a gas stream. In one approach, the saturation chamber 38 may be lined or packed with a porous material 51 such as a polyvinyl alcohol sponge, or cotton in order to wick the vaporized working fluid 48 to the entire interior surface of the saturation chamber 38 thereby improving the efficiency of the saturation process. Additionally, a recirculation pump (not shown) could maintain the circulation of working fluid 48 through the saturation chamber 38. In this way a constant volume of working fluid 48 is maintained within the saturation chamber 38. In addition, in this system the working fluid 48 can be continuously cleaned by passing it through a separate recirculation filter (not shown). Another approach would simply be to use a static pool of working fluid. Essentially, this idea could be implemented using the above described saturation chamber 38 without the associated elements for recirculating the working fluid 48.

The saturation filter 44 can be made of any suitable material, preferably a sintered metal filter such as used for high-purity gas lines as an all metal construction lends itself to being maintained at a known and controlled temperature. Examples of suitable filters are the Gas Shield Penta Filter manufactured by Mott Corporation or the Ultipor filter by Pall. Those skilled in the art will recognize that other types of filters, such as, HEPA filters would work as well in the FMCNC 10. The saturation filter 44 may be incorporated into the same structure as saturation chamber 38 or may be separate. Although FIG. 6 depicts a preferred embodiment of the present invention wherein the saturation filter 44 is mounted at the saturation chamber inlet 40, the filter could also be positioned at the outlet of the saturation chamber 42. In a preferred embodiment, the saturation filter 44 is positioned at the saturation chamber inlet 40 and is contained within the same housing as the saturation chamber 38, as shown in FIG. 6. In one embodiment the saturation filter 44 is in thermal communication with a second temperature controller 52 and is heated to a temperature $T_2$ such that the vaporized working fluid 48 in the vapor-laden gas flow 32 does not condense in the saturation filter 44. Preferably $T_2$ is no less, and is preferably 5 to 15° C. greater than, temperature $T_1$.

The vapor-laden gas flow 32 exits the saturation chamber outlet 42 and enters the mixing chamber inlet 26. The particles to be measured are carried in a sample gas flow 34 which enters mixing chamber 12 through the sample gas nozzles 28. To encourage condensation the sample gas flow 34 is held at a lower temperature $T_3$ than the vapor-laden gas flow 32. Preferably $T_3$ is about room temperature, although the sample gas source 14 could also comprise a cooler (not shown) to chill the sample gas flow 34 below room temperature. The two gas flows, 32 and 34, are mixed in mixing chamber 12 to produce a mixed gas flow 54 wherein the mixed gas is supersaturated with respect to the working fluid. In general, the mixing of the vapor-laden gas flow 32 at a relatively high temperature $T_1$ and the sample gas flow 34 at a relatively low temperature $T_3$ results in the supersaturation of the mixed gas flow 54.

Referring specifically to FIG. 6, in one embodiment the FMCNC 10 includes a growth tube 56 adapted to allow gas to flow therethrough and having an inlet 58 and an outlet 60. The growth tube inlet 58 is in fluid communication with the mixing chamber outlet 30 such that the mixed gas flow 54 exits the mixing chamber 12 through the mixing chamber outlet 30 and enters the growth tube 56 through the growth tube inlet 58. As the mixed gas flow 54 moves through the growth tube 56, particles entrained in the mixed gas flow 54 operate as nucleation sites for condensation of the vaporized working fluid 48 to grow the particles to a larger size. The growth tube 56 may have any length which provides suitable time for the vaporized working fluid 48 to condense on the particles. For example, in the embodiment shown in FIG. 6 the growth tube 56 is about 7 cm long, however, other lengths can be used so long as the particle loss due to thermophoretic reactions with the walls of the growth tube 56 is minimized.

To encourage condensation and minimize growth tube length, the interior of the growth tube 56 can be cooled by a cooling device 62. Cooling of the growth chamber may be achieved by using thermo-electric devices (TED). TED are electrical solid-state devices such as the model CPI.4-127-045L manufactured by Melcor. Other cooling means are also possible such as recirculating a refrigerant fluid, cooled to the desired temperature, around the growth tube 56. To achieve a uniform temperature in growth tube 56, it is preferably constructed from a high thermal conductivity material such as copper. Additionally, in this embodiment, an insulator 64 insulates the growth tube 56 from the room-temperature particle detector 18. Any suitable insulating material, such as Delrin can be used to form the insulator 64.

The grown particles are drawn from the growth tube outlet 60 and enter the particle detector 18 where well known techniques are used to detect the size and number of grown particles. In a preferred embodiment, shown in FIG. 6, the particle detector 18 is located proximal to growth tube 56 so as to avoid the condensation of vapor on the walls of the growth tube 56 and to minimize particle loss to walls before they are counted by particle detector 18. The number of grown particles is detected within the particle detector 18. Any suitable detection device could be used as a particle detector 18, for example, light-scattering particle detectors are well-known to those skilled in the art of particle detectors. Suitable devices which could be used as light-scattering particle detectors include a modified version of Model LPSC-310 laser particle counter manufactured by Particle Measuring Systems, Inc. The standard Model LPSC-310 laser particle counter is calibrated for a 1.0 cfm sample flow rate. For use in FMCNC 10, the laser particle counter is calibrated for a sample flow rate of about 0.65 l/min.

In one embodiment, the gas flow is drawn through the FMCNC 10 by a pump 66. The pump 66 draws gas from a gas source 46 into the FMCNC 10. The vapor-laden and sample gas flows are drawn through the FMCNC 10, through the particle detector 18 to the vacuum pump 66, and are exhausted through the exhaust 68. The exhaust 68 may be connected to a process line (not shown) or may operate to exhaust the mixed gas stream 54 into the environment. The gas flow through the pump 66 is controlled by a flow control valve 70, which opens and closes as appropriate to maintain the desired flow rate of gas through the pump 66. Those skilled in the art of CNC's recognize that there are many other methods to achieve flow control. In one embodiment of the present invention, the saturated gas flow rate, through pump 66 is 1.0 l/min and the sample gas flow rate through is 0.65 l/min. Although a vacuum pump 66 is shown in this embodiment, any pressure or vacuum producing device that creates a pressure differential between the sample gas source supply 14 and the detector 18 can be used. Examples of suitable, commercially available vacuum pumps are the Gast Model 2032-V103 or the KNF Neuberger model MPU860 Diaphragm pump.

The FMCNC of FIG. 7 comprises the elements discussed above, and additionally, a vapor-laden gas distribution manifold 72 disposed between the saturation filter 44 and the saturation chamber 38, comprising a saturation chamber flow controller 74, and a bypass flow controller 76. The vapor-laden gas distribution manifold 72 is constructed so that gas passing through the saturation filter 44 is variably divided by the flow controllers 74 and 76 so that some portion of the gas enters the saturation chamber 38, and some portion enters a bypass conduit 78. The gas passing through the saturation chamber 38 interacts with the vaporized working fluid 48 as described above and emerges from the saturation chamber outlet 42 as a vapor-laden gas into a vapor-laden gas mixing chamber 80. The gas passing through the bypass conduit also emerges into the vapor-laden gas mixing chamber 80 but is not vapor-laden. The vapor-laden gas and the bypass gas mix in the vapor-laden gas mixing chamber 80 and then enter the mixing chamber 12 through the mixing chamber inlet 26 as a flow of vapor-laden gas 32. In the embodiment shown, the bypass conduit runs through the heated region of the saturation chamber 38 such that the bypass gas is maintained at the same temperature as the vapor-laden gas, however, the bypass conduit could also be designed with an independent temperature controller.

The vapor-laden gas distribution manifold 72 can be constructed by any suitable means such that by variably adjusting the relative flows of gas through the flow controllers 74 and 76, the ratio of vapor-laden gas to sample gas in the mixing condensation chamber can be altered. The speed at which supersaturation is achieved and the critical size of the particles needed to condense out the vaporized working fluid 48 are critically dependent on the molar ratio of vapor to sample gas, by altering the ratio of vapor-laden gas to non-vapor-laden gas the critical particle size needed for condensation and the speed at which supersaturation and condensation can be achieved can be controlled. Further, because the ratio can be altered by adjusting the flow controllers 74 and 76, the detectable particle size can be scanned and the speed of the scan can be adjusted far more efficiently than can be achieved by varying other parameters of the system, such as, temperature.

Another embodiment of the sample gas source 14 is shown in detail in FIG. 8. In this embodiment the sample gas source 14 comprises a nebulizer 82 for producing a fine mist of any chosen sample gas. The nebulizer 82 is in fluid communication with a tube furnace 84 to dry the nebulized sample aerosol. The tube furnace 84 is adapted to allow the sample gas to flow therethrough. The tube furnace is in thermal contact with a furnace heater 85 which heats the furnace to temperatures needed to dry the nebulized sample aerosol. The temperature of the furnace will depend on the sample aerosol chosen, for example, for a nebulized mist of NaCl, a furnace temperature of about 700° C. is utilized. The gas exits the tube furnace 84 through an outlet 86, which is intersected by at least one quenching jet 88, providing a source of filtered air such that the quenching jet 88 injects filtered air into the outlet 86 of the tube furnace 84 at a specified injection rate to cool the heated gas. Any suitable injection rate can be used, in one preferred embodiment, filtered air is injected at a rate of 20 l/min. A neutralizer 90, designed to neutralize the aerosol particles, is disposed between the tube furnace outlet 86 and a DMA classifier 92. After passing through the neutralizer 90, the DMA classifier 92 then sorts the particles based on their size to produce a monodisperse, ultrafine sample gas source 14 of specified particle size. Any suitable neutralizer 90 and DMA 92 can be used. In a preferred embodiment, the charger 90 is a $^{210}$Po charger and the DMA classifier 92 is a radial DMA classifier. The monodisperse, ultrafine sample gas source 14 then enters the FMCNC 10 as described above.

Control of the various temperature controllers 50 and 52, as well as control of flow controllers 70, 74 and 76 is accomplished using well-known Proportional, Integral, Derivative (PID) controllers. For example, in a preferred embodiment of the present invention, a LabView PID controller from National Instruments is used to control each of the temperatures in FMCNC 10. As is known to those skilled in the art of PID controllers, the user sets a setpoint for each control variable and the PID controller outputs a control signal that controls the operation of the selected device as appropriate to maintain the setpoint. Those skilled in the art of CNCs will recognize there are other control methods which may also be used.

Figure 9:
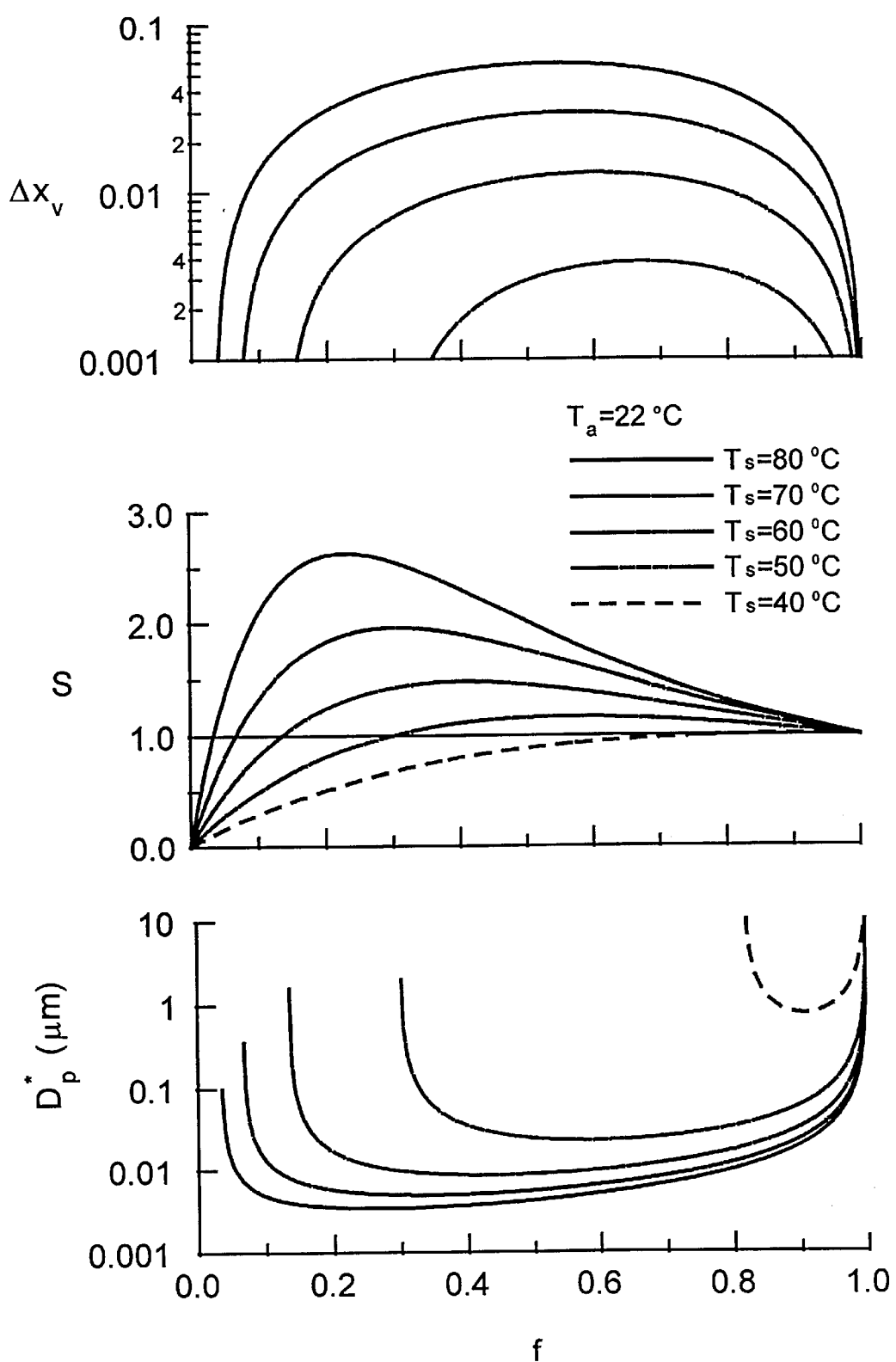
FIG. 9 is a graphical analysis of the effect increased temperature has on the scanning parameters of the fast mixing condensation nucleus counter according to the invention.
Figure 10:
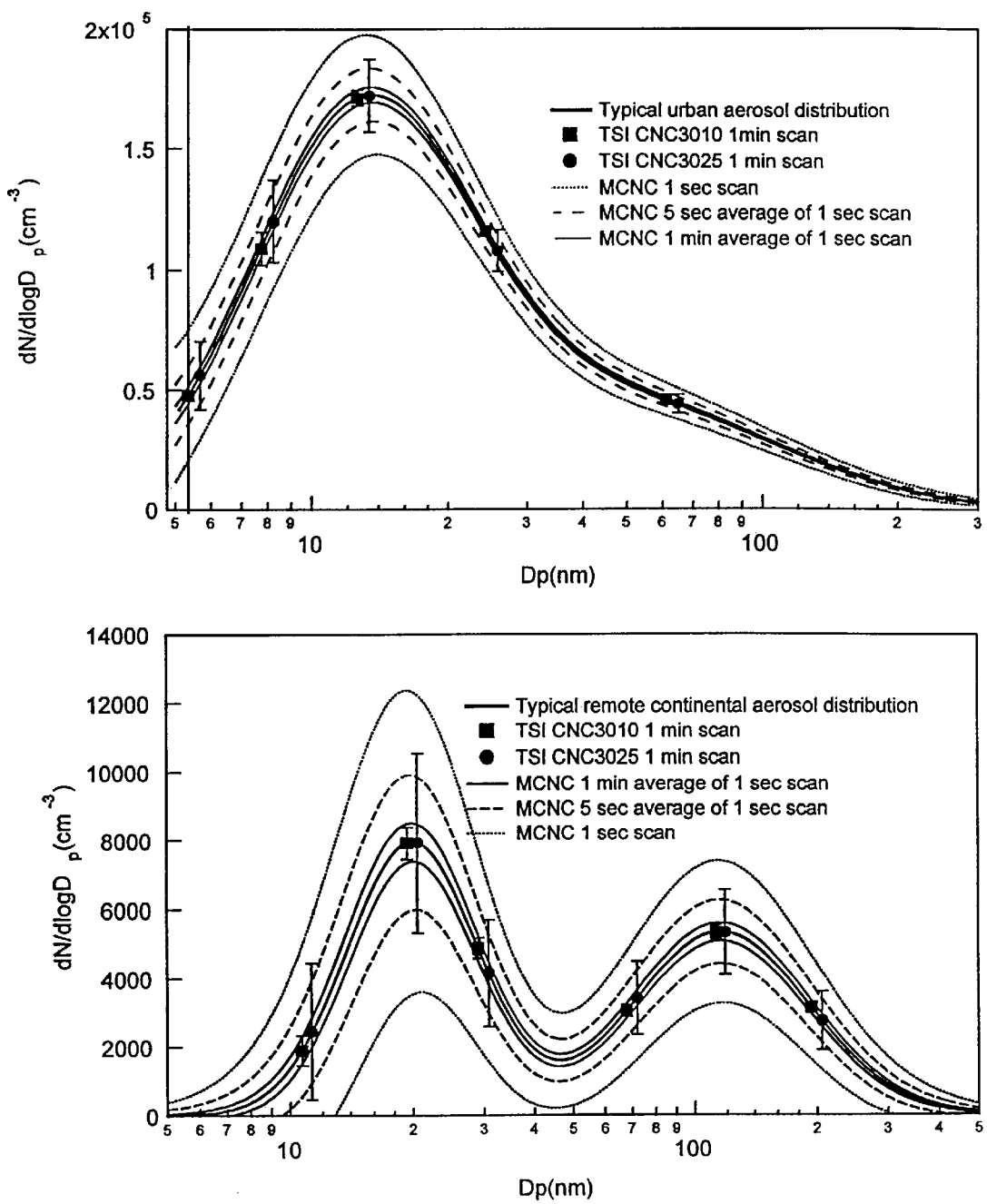
FIG. 10 is a graphical comparison of the scanning parameters of the prior art and the present invention.

A prototype of the FMCNC 10 described above was constructed according to the design detailed in FIG. 6 utilizing a mixing chamber 12 as described and shown in FIG. 3 above. Table 1 and FIGS. 9 and 10 show the results of tests comparing the scanning speed and efficiency of this embodiment of the FMCNC of the present invention with that of the prior art CNCs. In the test FMCNC, an initial flow of sample gas is split and a fraction of the flow is passed through a HEPA filter, to remove all particles, and then through a packed bed saturation chamber of cotton saturated with n-butanol. The saturation chamber was maintained at a pre-determined temperature between 40 and 80° C. using a PID. The sample gas bypassing the saturation chamber was held at room temperature.

The sample gas entered through two nozzles aligned antipodal to each other and having an internal diameter of 0.7 mm. Polymeric tubes coupled the nozzles to the mixing chamber to minimize thermal coupling prior to mixing. The vapor-laden gas emerged through an inlet aligned transverse to the nozzles. The flows were then turbulently mixed in a small mixing chamber having a total volume of about 0.85 cm$^3$. The mixed gas exited the mixing chamber and flowed down a ¼ inch copper growth tube having an internal diameter of 0.48 cm and a length of 7 cm to the detector. The flow rate to the detector was maintained at 1.0 l/min, a LabView PID controller controlled the flow rate with an accuracy of 0.2%.

Typically, CNCs have operated at a temperature where the vapor mole fraction is just slightly above that which is needed to achieve supersaturation. It was thought that increasing the temperature further would cause delays in condensation times and unwanted reactions with the walls of the mixing chamber. As shown in FIG. 9, the present invention uses a higher saturation chamber temperature than is typically used, which yields a large excess vapor mole fraction $\Delta\chi_v$ and saturation ratio S, and which, surprisingly, also allows for condensation of the working fluid on particles of smaller initial size. In turn, these improved operational conditions yield faster supersaturation and condensation times.

The mixing times of the FMCNC of the present invention and the two prior art CNCs, manufactured by TSI, were measured using a pulse of ultra-fine particles created by a single discharge in a spark-source aerosol generator. Additionally, the FMCNC counting efficiency for ultrafine aerosol particles was measured. Particles ranging from 5 nm to 150 nm were measured. These results were compared with published values for the counting efficiency of the commercially available TSI 3010 CNC and TSI 3025 UCNC. The aerosol flow (Qa), total gas flow ($Q_{total}$), the total delay time ($\tau_{delay}$), the mixing delay time ($\tau_{mixing}$), and the critical particle size, or the particle size at which the counting efficiency is 50% for all three machines is reported.

The results of this experiment are shown in Table 1, below.

TABLE 1

Flows, Delay Times, Minimum Detectable Particle Size Comparison for FMCNC, TSI 3010 CNC and TSI 3025 UCNC

| CNC Type | Q Aerosol (l/min) | Q total (l/min) | τ delay (s) | τ mixing (s) | $D_{p,50\%}$ (nm) |
|---|---|---|---|---|---|
| FMCNC | 0.65 | 1 | 0.38 ± 0.013 | 0.058 ± 0.002 | 5 |
| TSI 3025 (high flow) | 0.03 | 1.5 | 1.03 ± 0.02 | 0.174 ± 0.005 | 3 |
| TSI 3025 (low flow) | 0.03 | 0.3 | 1.7 | 1 | 3 |
| TSI 3010 (enhanced) | 1 | 1 | — | 1.35 ± 0.05 | 3.5 |
| TSI 3010 | 1 | 1 | 1.2 | 0.9 | 10 |

As Table 1 shows, the total delay time for the FMCNC is only 0.38 s, compared to a 1.03 s delay time for the fastest prior art device, the TSI 3025 UCNC. It was previously thought that small mixing chamber volumes would result in increased particle losses because of thermophoretic deposition of the netrained particles to the walls of the mixing chamber. As shown in Table 1 and FIG. 10, and discussed in more detail below, surprisingly, the opposite has been found to be true, as the smaller mixing chamber volumes described herein have reduced overall residence time of the particles within the mixing chamber and thus allowed shorter overall scan times.

The minimum detectable particle size is not significantly different between the three instruments, 5 nm for the FMCNC and 3 nm for the TSI 3025 UCNC. It should be noted that these measurements were taken without a fully optimized FMCNC, thus the minimum detectable particle size is expected to be improved in the most recent embodiment of the invention. Further, it is well-known to those skilled in the art of CNCs that the CNC's detectable range can be extended to sub-nanometer sizes by carefully controlling the temperatures of the saturated vapor and aerosol flows to ensure adiabatic operation.

It is noteworthy, however, that the aerosol flow rate for the FMCNC of the present invention is 17 times that of the fastest response laminar flow CNCs. This aerosol rate translates into larger count rates at a given DMA scan or, conversely, into equal numbers of particles counted in each channel for much shorter scans.

FIG. 10 shows a comparison of the reliability of fast particle distribution scans made using the FMCNC of the present invention and the prior art CNCs. The expected number of particles counted during scanning DMA measurements is the product of the volumetric flow rate of aerosol that is counted, the number concentration of particles in the transmitted particle size interval, and the probability that particles in that interval will be charged and transmitted through the DMA to the CNC. Thus, the uncertainties in the measurements are accentuated in fast scans due to unavoidable degradation of the counting statistics. FIG. 10 examines the performance of the FMCNC at typical urban and remote continental (background or ambient) aerosol concentrations. As shown, under either condition the uncertainty in a 1 s scan using the FMCNC exceeds that of a 1 min scan using either the TSI 3025 or TSI 3010. However, a 5 s average of 1 s scans using the FMCNC outperforms the TSI 3025, and a 1 min average of 1 s scans matches the TSI 3010.

The advantage from such fast scans is that DMA size distributions are measured by scanning or stepping through a range of particle sizes. Each particle size is thus measured at a different time. Fast scans reduce the time lag between measurements of different particle sizes. In measurements made aboard moving platforms, e.g. road-side or tunnel measurements of vehicle emissions, this time-averaging eliminates biases and misinterpretation that occur when the instrument transits from one air mass to another.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A fast mixing condensation nucleus counter for detecting particles entrained in a sample gas stream, said counter comprising:
   a mixing condensation device having:
      a mixing chamber;
      an inlet for introducing a vapor-laden gas flow to the chamber;
      an outlet for extracting the mixture from the chamber
      at least one nozzle for introducing a sample gas flow to the chamber in mixing proximity to the vapor-laden gas flow such that the particles flow through the chamber from said at least one nozzle to the outlet;
      wherein the inlet and said at least one nozzle are arranged such that the vapor-laden gas flow and the sample gas flow interact to create a turbulent flow of a mixture thereof within the chamber at a Reynolds number of less than about 2200; and
      the mixing chamber defines a volume sufficiently small to ensure that the particles move from said at least one nozzle to said outlet at a substantially uniform relative velocity without forming recirculation currents; and
   a particle detector for receiving the mixture from the outlet and sensing a characteristic of said mixture.

2. The fast mixing condensation nucleus counter as recited in claim 1 wherein said counter further comprises a sample gas distribution manifold disposed at the entrance to said at least one nozzle, said manifold having a plurality of channels extending from said manifold, with said plurality of channels positioned with respect to said at least one nozzle to evenly divide said sample gas stream into a plurality of flows, with each of said flows entering said at least one nozzle.

3. The fast mixing condensation nucleus counter as recited in claim 2 wherein the mixing condensation chamber comprises two nozzles.

4. The fast mixing condensation nucleus counter as recited in claim 3 wherein the nozzles are aligned antipodal to each other.

5. The fast mixing condensation nucleus counter as recited in claim 3 wherein the nozzles are aligned transverse to the vapor-laden gas inlet.

6. The fast mixing condensation nucleus counter as recited in claim 3 wherein the inlet and the nozzle are aligned in opposing tangential directions.

7. The fast mixing condensation nucleus counter as recited in claim 1 wherein the nozzles are coupled to the mixing condensation chamber through a polymeric tubing.

8. The fast mixing condensation nucleus counter as recited in claim 1 wherein the mixing chamber has a cross section and wherein the inlet has a diameter substantially the same as the cross section of the inner cavity.

9. The fast mixing condensation nucleus counter as recited in claim 1 wherein the vapor-laden gas inlet is coupled to the mixing condensation chamber through a polymeric tubing.

10. The fast mixing condensation nucleus counter as recited in claim 1 wherein the inner cavity has a volume of from 0.25 and 1.00 cm$^3$.

11. The fast mixing condensation nucleus counter as recited in claim 1 wherein the inner cavity has a volume of about 0.85 cm$^3$.

12. The fast mixing condensation nucleus counter as recited in claim 1 wherein the particle detector is an optical particle detector.

13. The fast mixing condensation nucleus counter as recited in claim 1 wherein the vapor-laden gas further has a vaporized working fluid entrained therein and a first temperature, and the sample gas has particles entrained therein and a second temperature, wherein said second temperature is less than said first temperature such that when said sample gas and said vapor-laden gas are mixed in the mixing condensation chamber, said vaporized working fluid condenses on said particles to produce enlarged particles.

14. The fast mixing condensation nucleus counter as recited in claim 1 wherein the counter further comprises a differential pressure means for causing said vapor-laden gas and said sample gas to flow into said fast mixing condensation nucleus counter.

15. The fast mixing condensation nucleus counter as recited in claim 1 wherein the counter further comprises a temperature control apparatus for maintaining the inner cavity of said mixing condensation chamber at a specified temperature such that the vapor-laden gas does not condense on the inner cavity.

16. The fast mixing condensation nucleus counter as recited in claim 1 wherein the counter further comprises a growth tube disposed between said mixing condensation chamber and said particle detector, said growth tube being adapted to allow the mixture to pass therethrough and having a length sufficient to allow the vapor-laden gas to condense on the particles of the sample gas to produce enlarged particles having a particle size sufficient for detection by the particle detector.

17. The fast mixing condensation nucleus counter as recited in claim 16 wherein the growth chamber further comprises a temperature control apparatus for maintaining the inside walls of said growth chamber at a specified temperature such that the mixture does not adhere to the growth tube.

18. The fast mixing condensation nucleus counter as recited in claim 1 wherein the counter further comprises a saturation chamber having an inlet, an outlet, and a first heating apparatus, and containing a vaporized working fluid, said first heating apparatus maintaining said saturation chamber at a first temperature such that a gas flowing through said saturation chamber becomes saturated with said vaporized working fluid to form a vapor-laden gas.

19. The fast mixing condensation nucleus counter as recited in claim 18 wherein the saturation chamber is a packed bed saturation chamber.

20. The fast mixing condensation nucleus counter as recited in claim 18 wherein the counter further comprises a saturation filter in fluid communication with the inlet of the saturation chamber which removes particles from said gas.

21. The fast mixing condensation nucleus counter as recited in claim 20 wherein said saturation filter comprises a second heating apparatus for maintaining said saturation filter at said first temperature.

22. The fast mixing condensation nucleus counter as recited in claim 20 wherein the counter further comprises a gas distribution manifold, said manifold evenly dividing said sample gas stream into a plurality of flows so that one of said flows enters said saturation filter of said saturation chamber, and one of said flows enters a conduit in direct fluid communication with the mixing condensation chamber.

23. The fast mixing condensation nucleus counter as recited in claim 22 wherein said counter further comprises a sample gas conditioner disposed within the conduit and adapted to allow said sample gas stream to flow therethrough said sample gas conditioner having a second temperature control apparatus for maintaining the temperature of said sample gas at the second temperature and a flow rate detector for measuring the flow rate of said sample gas.

24. The fast mixing condensation nucleus counter as recited in claim 20 further comprises:
   a pre-saturation gas distribution manifold disposed between said saturation filter and said saturation chamber, said manifold variably dividing said sample gas stream into a plurality of flows so that one of said flows enters said inlet of said saturation chamber, and one of said flows enters a bypass conduit, said bypass conduit having a third heating apparatus which maintains the bypass conduit at the first temperature; and
   a saturation mixing chamber having at least one inlet and an outlet, said at least one inlet being in direct fluid communication with the outlet of the saturation chamber and the bypass conduit and said outlet being in direct fluid communication with the inlet of the mixing condensation chamber;
   wherein the ratio of vapor-laden gas to sample gas in the mixing condensation chamber by variably controlling the flow of gas into the saturation chamber.

25. The fast mixing condensation nucleus counter as recited in claim 1 wherein the sample gas is generated in a sample gas source comprising:
   a nebulizer having an inlet and an outlet, said nebulizer producing a constant ultrafine sample gas flow rate;
   a tube furnace having an inlet and an outlet, said furnace inlet in fluid communication with the outlet of the nebulizer, said outlet defining conduit having a center axis, said tube furnace having a furnace temperature controller that maintains the tube furnace at a constant furnace temperature;
   a furnace quencher having at least one quenching jet aligned radially around the center axis of the tube furnace outlet, said quenching jet provided with a source of filtered air such that the quenching jet can inject the filtered air into the outlet of the tube furnace at a specified injection rate;
   an ultrafine sample gas DMA classifier having an inlet and an outlet, said outlet in fluid communication with the saturation chamber, said classifier provided to produce a monodisperse ultrafine sample gas of specified particle size;
   a charger disposed between the outlet of the tube furnace and the inlet of the classifier.

26. The fast mixing condensation nucleus counter as recited in claim 1, wherein the counter is a component of a scanning electrical mobility spectrometer.

27. A fast mixing condensation nucleus counter for detecting particles entrained in a sample gas stream, said counter comprising:
   a mixing condensation device having:
      a mixing chamber;
      an inlet for introducing a vapor-laden gas flow to the chamber;
      an outlet for extracting the vapor-laden gas flow from the chamber;
      at least one nozzle for introducing a sample gas flow to the chamber in mixing proximity to the vapor-laden gas flow such that the particles flow through the chamber from said at least one nozzle to the outlet;
      wherein the mixing chamber has a cross section and wherein the inlet has a diameter substantially the same as the cross section of the inner cavity; and
      wherein the inlet and said at least one nozzle are arranged such that the vapor-laden gas flow and the sample gas flow interact such that the kinetic energies of the flows are dissipated within the mixing chamber to create a turbulent flow of a mixture thereof even at a Reynolds number of less than about 2200 such that adjacent particles within said gas flow move through said chamber substantially together and substantially without forming recirculation currents; and
   a particle detector for receiving the particles from the outlet and sensing a characteristic of said particles.

28. A method of analyzing particles entrained within a sample gas comprising introducing a sample gas having particles entrained therein into the fast mixing condensation nucleus counter of claim 1.

* * * * *

UNITED STATES PATENT AND TRADEMARK OFFICE
CERTIFICATE OF CORRECTION

PATENT NO. : 6,567,157 B1
DATED : May 20, 2003
INVENTOR(S) : Flagan et al.

It is certified that error appears in the above-identified patent and that said Letters Patent is hereby corrected as shown below:

Title page,
Item [56], References Cited, OTHER PUBLICATIONS, "Agarwal, J.K. and Sem, G.J." reference, delete "Areosol", insert -- Aerosol --
"Bartz, H., Fissan, H., and Liu B.Y.H.," reference, delete "Aerosal", insert -- Aerosol --
"Kousaka, Yasuo, et al." reference, delete "119 123", insert -- 119-123 --

Column 17,
Line 33, before "by", insert -- can be adjusted --

Column 18,
Line 9, after "specified particle size;", insert -- and --

Signed and Sealed this

Second Day of August, 2005

JON W. DUDAS
*Director of the United States Patent and Trademark Office*